US006825318B2

United States Patent
Kim et al.

(10) Patent No.: US 6,825,318 B2
(45) Date of Patent: Nov. 30, 2004

(54) MIMETIC PEPTIDES FOR AN EPITOPE OF APOLIPOPROTEIN B-100, CONCATEMERS OF THE PEPTIDES, AND MODIFIED PEPTIDES, AND COMPOSITIONS COMPRISING THE SAME

(75) Inventors: Hyo-Joon Kim, 3-1001, Sunkyung APT, Sungpo-dong, Ansan-si, Kyunggi-do (KR), 425-040; Hae-Jung Joung, Seoul (KR)

(73) Assignee: Hyo-Joon Kim, Kyunggi-do (KR)

( * ) Notice: Subject to any disclaimer, the term of this patent is extended or adjusted under 35 U.S.C. 154(b) by 0 days.

(21) Appl. No.: 10/378,707

(22) Filed: Mar. 4, 2003

(65) Prior Publication Data

US 2003/0211997 A1 Nov. 13, 2003

Related U.S. Application Data

(63) Continuation of application No. PCT/KR01/01492, filed on Sep. 4, 2001.

(30) Foreign Application Priority Data

Sep. 4, 2000 (KR) .................................. 2000-0052055
Sep. 4, 2001 (KR) .................................. 2001-0054005

(51) Int. Cl.[7] ........................ A61K 38/00; A61K 38/04; C07K 16/00; C07K 17/00; C07K 5/00; C07K 7/00

(52) U.S. Cl. ...................... 530/326; 530/300; 530/350; 435/69.1

(58) Field of Search ................................ 530/350, 359, 530/324, 300, 357; 514/12; 435/7.1, 7.23, 69; 424/135.1

(56) References Cited

FOREIGN PATENT DOCUMENTS

WO      WO98/39469      *   9/1998

OTHER PUBLICATIONS

Ahn, Sang Hoon, Naturally Occuring Mutations Near Pre-core Translational Initiation Site Reduce Hepatitis B E Antigen Production. Heptology, (Oct., 2002) vol. 36, No. 4 Part 2, pp. 370A.*

Alving CR et al., 1999, "Naturally occurring antibodies to cholesterol: a new theory of LDL cholesterol metabolism" *Immunol Today* 20(8):362–366.

Ruihua W et al., 1999, "Autoantibodies to OxLDL are decreased in individuals with borderline hypertension" *Hypertension*, 33:53–59.

Stadler BM et al., 1999,"Mimotope and anti–idiotypic vaccines to induce an anti–IgE response" *Int Arch Allergy Immunol* 118(2–4):119–121.

(List continued on next page.)

*Primary Examiner*—Robert A. Wax
*Assistant Examiner*—Robert B. Mondesi
(74) *Attorney, Agent, or Firm*—Baker Botts LLP

(57) ABSTRACT

The present invention relates to a vaccine composition for treatment of obesity. More particularly, the present invention is directed to a vaccine composition which comprises a mimetic peptide epitope of apolipoprotein B-100, concatemers of said memetic peptide, and/or modified memetic peptides.

13 Claims, 12 Drawing Sheets

OTHER PUBLICATIONS

Dalum I et al., 1997, "Induction of cross–reactive antibodies against a self protein by immunization with a modified self protein containing a foreign T helper epitope" *Molecular Immunology*, 34(16–17):1113–1120.

Wu JT et al., 1997, "Autoantibodies against oxidized LDL: A potential marker for atherosclerosis" *Clinics In Laboratory Medicine*, 17(3):595–604.

Alving CR et al., 1996, "Antibodies to cholesterol: Biological implications of antibodies to lipids" *Curr Top Mocrobid Immunol*, 210:181–186.

Alving CR et al., 1996, "Immunization with cholesterol–rich liposomes induces anti–cholesterol antibodies and reduces diet–induced hypercholesterolemia and plaque formation" *J Lab Clin Med*, 127(1):40–49.

Soued M et al., 1996, "Chylomicron remnant uptake by enterocytes is receptor dependent" *Am J Physiol* 270(1 Pt 1):G203–G212.

Palinski W et al., 1995, "Immunization of low density lipoprotein (LDL) receptor–deficient rabbits with homologous malondialdehyde–modified LDL reduces atherogenesis" *Proc. Natl. Acad. Sci USA*, 92:821–825.

Steward MW et al., 1995, "A mimotope from a solid–phase peptide library induces a measles virus–neutralizing and protective antibody response" *J Virol* 69(12):7668–7673.

Bailey JM et al., 1994, "Cholesterol vaccines" *Science*, 264:1064–1068.

Young SG, 1990, "Recent progress in understanding apolipoprotein B" *Circulation* 82(5):1574–1594.

Alving CR et al., 1989, "Naturally occurring autoantibodies to cholesterol in humans" *Biochemical Society Transactions*, 17:637–639.

Knott TJ et al., 1986, "Complete protein sequence and identification of structural domains of human apolipoprotein B" *Nature* 323(6090):734–738.

Brown MS et al., 1983, "Lipoprotein metabolism in the macrophage: Implications for cholesterol deposition in Atherosclerosis" *Ann. Review Biochem*, 52:223–261.

\* cited by examiner

A.

MIMETIC PEPTIDES FOR AN EPITOPE OF APOLIPOPROTEIN B-100, CONCATEMERS OF THE PEPTIDES, AND MODIFIED PEPTIDES, AND COMPOSITIONS COMPRISING THE SAME

This application is a continuation of International PCT Application No. PCT/KR01/01492 filed on Sep. 4, 2001 and published in English as WO 02/20040 on Mar. 14, 2002, which claims the benefit of Korean Application Nos. 2000/0052055 and 2001/0054005 filed on Sep. 4, 2000 and Sep. 4, 2001 respectively.

BACKGROUND OF THE INVENTION

Blood serum lipids include cholesterol, triglycerides (TG), free fatty acid, phospholipid and the like, and exist in blood stream in the form of lipoproteins which are complexes of lipid and apolipoprotein.

Of these lipoproteins, low density lipoprotein (LDL) is the major carrier for TG and cholesterol. The number of patients suffering from arteriosclerosis, coronary artery disease, or cardiac infarction caused by elevated LDL-cholesterol level in blood has increased considerably due to changes in diet or other factors.

Research has focused on elucidating the etiology of the above-identified diseases and discovering methods for lowering the level of LDL-cholesterol in patients suffering from these diseases.

LDL-cholesterol, a major etiological factor for adult disease related to lipid metabolism, may be converted to high density lipoprotein (HDL) by macrophages. In addition, LDL-cholesterol may be converted to another material or be converted to bile acid in the liver (Brown, M. S. and Goldstein, J. L., 1983, Annu. Rev. Biochem., 52: 223–261).

Apolipoprotein B-100 is a major protein part of LDL and exists also in very low density lipoprotein (VLDL) and chylomicron. LDL-cholesterol in blood may be removed through phagocytosis by macrophages where an antibody in the blood stream is induced by recognizing the apolipoprotein B-100, since apolipoprotein B-100 leads LDL particles to bind to LDL-receptors exposed on the cell surface (Dalum I., et al., 1997, Mol. Immunol., 34 (16–17): 1113–20).

Where a macromolecule, such as an antibody, is bound to apolipoprotein B-100, which exists on the surface of LDL, lipases, such as lipoprotein lipase, cannot hydrolize TG and the like due to steric hindrance caused by the macromolecule bound to apolipoprotein B-100. Consequently, the formation of free fatty acid, a major factor for obesity, can be inhibited by means of the antibody which can bind to apolipoprotein B-100.

Recently, vaccine-based methods for lowering LDL-cholesterol and for inhibiting the outbreak of arteriosclerosis have been tried in various animal models such as mouse and rabbit. For example, C. R. Alving reported that cholesterol may be modified by metabolites or its oxidation and that the modified cholesterol can be a strong antigenic determinants in some cases (Alving, C. R., et al., 1989, Biochem. Soc. Trans., 17 (4): 637–9; Alving, C. R., et al., 1996, J. Lab. Clin. Med., 127: 40–49; Alving, C. R., et al., 1996, Curr. Top. Microbiol. Immunol., 210: 181–6).

Furthermore, it has been reported that an endogenous antibody for cholesterol exists in blood serum (Wu, J. T., L. L., 1997, Clin. Lab. Med., 17 (3): 595–604, Review). It has also been reported that hypercholesterolemia and arteriosclerosis are remarkably reduced in rabbits injected with cholesterol-containing liposomes followed by maintenance on cholesterol-containing meal relative to control rabbits that were maintained on the same diet, but did not receive the liposomes.

The antibody induced by cholesterol vaccination is immunoglobin M (IgM), which binds to VLDL, intermediate density lipoprotein (IDL) and LDL. Based on the above, it is believed that a vaccine for treatment or prevention of hyperlipoidemia or arteriosclerosis caused by high level of cholesterol, will be possible (Bailey, J. M., 1994, Science, 264: 1067–1068; Palinski, W. et al., 1995, Proc. Natl. Acad. Sci. USA., 92 (3): 821–5; Wu, R. et al, 1999, Hypertension, 33 (1): 53–9).

The present inventors have found that obesity can be effectively prevented by mimetic peptide epitopes of apolipoprotein B-100, and based on the above, have developed a vaccine composition for treatment of obesity.

SUMMARY OF THE INVENTION

Therefore, some embodiments of the present invention provide a mimetic peptide for the epitope of apolipoprotein B-100, concatemers of the peptide, and modified peptides.

Additionally, some embodiments of the present invention provide a process for preparing the above mimetic peptide for the epitope of apolipoprotein B-100, concatemers of the peptide, and modified peptides.

Some embodiments of the present invention provide a vaccine composition for treatment or prevention of obesity, which comprises the above mimetic peptide for the epitope of apolipoprotein B100, concatemers of the peptide, and modified peptides.

Mimetic peptides for the epitope of apolipoprotein B-100 of the present invention may be selected from peptides of SEQ ID NO:1, SEQ ID NO:2, SEQ ID NO:3 or the mixtures thereof.

The invention further provides a method for preparing mimetic peptide, concatemers of the peptide, and modified peptides, which comprises: i) a step for inserting DNAs which encodes the above mimetic peptide, concatemer of the peptide or modified peptide into a vector, ii) a step for transforming the above vector into host cells, and then incubating them, and iii) a step for isolating the above mimetic peptide, concatemer or modified peptide from the above host cells.

BRIEF DESCRIPTION OF THE DRAWINGS

FIG. 1A represents the structure of leader cassette, FIG. 1B represents the structure of LB cassette, FIG. 1C represents the structure of BL cassette and FIG. 1D represents the structure of pBX4 expression vector.

DETAILED DESCRIPTION OF THE INVENTION

Figure 1A:
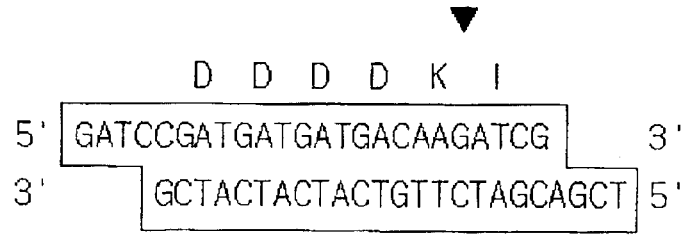
FIGS. 1A to 1D represent the structures and compositions of vector for expressing the mimetic peptide of the present invention.
Figure 1B:
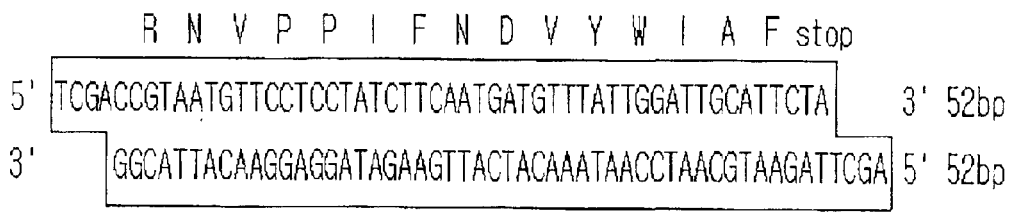
Figure 1C:
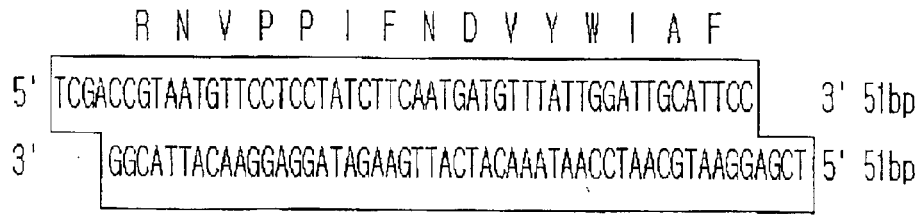
Figure 1D:
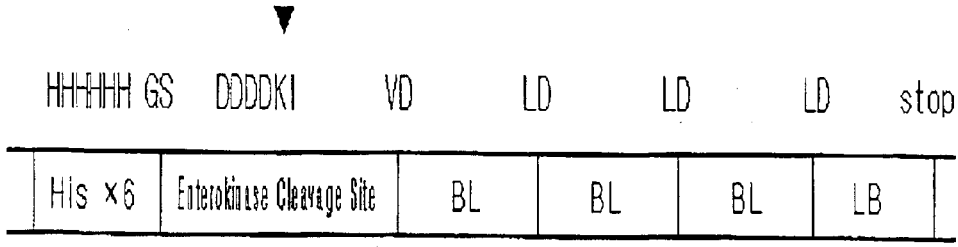

Hereinafter, the present invention will be described in more details. However, the present invention explained in below, is given only for the explanation of embodiment of the present invention and not intended to limit the scope of the present invention.

A peptide library system of phage was employed in the present invention in order to screen for an epitope of human apolipoprotein B-100 bound by monoclonal antibody (MabB23). Mimetic peptides structurally similar to antigenic determinants recognized by the antibody were identified and subsequently synthesized according to the amino acid sequence of the identified peptide.

Peptide library system is a kind of process for searching a three dimensional form of antigenic determinant. That is, DNA fragments which encode random-sequenced peptides are inserted into DNAs which encodes minor coat protein of phage, inserted into RF (Reading frame) DNA, and transformed to *E. coli* in order to express them. The peptides expressed on the surface of *E. coli* are reacted with antigen in order to screen the peptides structurally similar to the antigenic determinant.

In order to prepare anti-serum, mice were immunized by introducing the above mimetic peptides. It was confirmed that the anti-serum thus obtained recognizes the original apolipoprotein B-100, mimetic peptides and LDL at the same times (Identification of Antigenic Determinants for the Murine Monoclonal Antibodies Against Apolipoprotein A-1 and Apolipoprotein B-100 by using Phage-displayed Random Peptide library, Chi-Hoon Kim, Hanyang Univ., 1997).

Mimetic peptides of the present invention may be used in the form of concatemers in order to improve their antigenic determinant. As a nonlimiting embodiment of the present invention, two or more mimetic peptides may be linked with each other. The concatemer composed of three (3) to fifteen (15) peptides is desirable. More preferably, concatemers of the present invention comprise four (4) peptides of SEQ ID NO:1.

"Concatemer" of the above mimetic peptide of the present invention, refers to a polymer wherein the ends of the above mimetic peptides are linked with each other.

"The modified peptide" of the above mimetic peptide of the present invention refers to mimetic peptides variants which can be recognized by monoclonal or polyclonal antibody for apolipoprotein B-100. Such variants include substitutions, deletions, additions, and chemical substitutions of one or more amino acids from the mimetic peptide of the present invention.

The vaccine composition of the present invention, which contains mimetic peptide for the epitope of apolipoprotein B-100, concatemers of the peptide and/or modified peptides may inhibit the occurrence of obesity without causing autoimmunity in an organism. Therefore, LDL-related circulatory disease can be treated by a vaccine of the present invention more effective than the transitory and high-priced conventional method in which a cholesterol metabolism-related enzyme was inhibited.

Formulation of the vaccine composition may be prepared through any conventional method with the mimetic peptide, concatemer or modified peptide of the present invention. In the process for preparing the formulation, preferably, the composition wherein the active compound mixed or diluted with immune adjuvant, drug for reinforcing immunity, carrier, excipient and diluent, is selected from the group consisting of tablet, pill, granule, powder, cachet, suspension, emulsion, liquid, syrup, aerosol, soft or hard gelatin capsule, sterilized liquid for injection, sterilized powder and the like.

Immune adjuvant which may be employed in the composition of the present invention, is a sort of proteins containing the epitope of T cell (e.g. surface protein of hepatitis B virus), inert carrier such as aluminum salt, bentonite, latex, acrylic particle and the like; hydrophobic antigen (e.g. lipid), water-oil and oil-water emulsions, depot former (e.g. polysaccharide), T cell activator such as PPD, polyadenine, polyuracil and the like; B cell activator (e.g. B cell mitogen), surfactant such as saponin, lysolecithin, retinal, quil A, liposome and the like; material for reinforcing activity of macrophage; and alternative pathway complement activators such as inulin, zymosan, endotozin, lebamisole, *C. parvum* and the like.

"Carrier protein" of the present invention means a pharmaceutically allowable material such as protein or aluminum salt which can transport the mimetic peptide, concatemers of the peptide, and modified peptides of the present invention through blood stream.

Aluminum salt, phenoxyethyl ethanol, water, physiological salt solution, lactose, dextrose, sucrose, sorbitol, manitol, calcium silicate, cellulose, methyl cellulose, amorphous cellulose, polyvinylpyrolidon, metylhydroxy bezoate, propylhydroxybezoate, talc, magnesium stearate and a mineral oil may be used as suitable carriers, excipients or diluents in the composition of the present invention.

In addition, the composition of the present invention may further comprise a filler, an anti cohesive agent, a lubricant, a moisturizer, a perfume, an emulsifier and an antiseptic.

The composition of the present invention may be formulated by conventional methods well-known in this field to induce immune response in mammals through one or more inoculations.

The vaccine composition for the treatment of obesity of the present invention may be administered through various routes such as oral, dermal, intradermal, venous or muscular administration, preferably, the intradermal administration.

The effective dose of the vaccine composition of the present invention is 0.1 to 10 μg (active peptide) per kg of body weight, preferably, 0.5 to 1.0 μg per kg. However, the actual dosage of the active principle of the vaccine composition may be determined depends on several factors such as condition of immunity, administration routes, condition of patient, age, sex, body weight and the like. Therefore, the ranges of the said dosage amount do not limit the scope of the present invention in any way.

The primary pharmaceutical effect of the vaccine composition of the present invention is to prevent or treat obesity. This may occur through a mechanism whereby a human antibody induced by a mimetic peptide, concatemer or modified peptide of the invention binds an epitope of apolipoprotein B-100 on the surface of LDL, and, thereby, sterically inhibits lipase from generating fatty acids, the major etiological factor for obesity.

In addition, vaccine compositions of the present invention have an effect also on suppressing hyperlipoidemia. This may occur by a mechanism wherein LDL is detected and removed easily by macrophages through opsonization caused by a human antibody induced by a mimetic peptide, concatemer or modified peptide of the invention and conjugated to the epitope of apolipoprotein B-100 on the surface of LDL.

Another pharmaceutical effect of the composition of the present invention is to prevent or treat obesity by inhibiting cellular accumulation of lipid as cholesterol of free fatty acids. This may occur by a mechanism wherein human antibody induced by a mimetic peptide, concatemer or modified peptide of the present invention binds to the epitope of apolipoprotein B-100 on the surface of LDL, and, thereby, prohibits LDL from binding specifically to LDL receptor exposed on cell surface.

EXAMPLE 1

Synthesis and Annealing of Oligonucleotide

The oligonucleotides were chemically synthesized at Genemed Synthesis, Inc. (San Francisco, Calif., USA) in accordance with the sequence requested from the present inventors. In order to phosphorylate the 5' end of oligonucleotides, 50 $\mu$L of 100 pmol/$\mu$L oligonucleotide was incubated with 10 $\mu$L of 10 mM ATP, 3 $\mu$L of 10U/$\mu$L T4 polynucleotide kinase (Takara, Otsu, Japan) and 7 $\mu$L of 10×kinase buffer for two (2) hours at 37° C.

Each of the 10 $\mu$L aliquots of above phosphorylated oligonucleotides were mixed together, heated at 80° C. for 5 min and then chilled very slowly to the room temperature thus were annealed to the specific pairing between complementary strands.

EXAMPLE 2

Ligation

Ligation mixture was prepared by mixing 1 $\mu$L of vector DNA, 5 $\mu$L of insert DNA, 1 $\mu$L of T4 DNA ligase (NEB, Beverly, Mass., USA), 1 $\mu$L of 10× enzyme reaction buffer solution (NEB, Beverly, Mass.) and 2 $\mu$L of distilled water, and then incubated at 16° C. during the night and then incubated.

EXAMPLE 3

Construction of pBX Expression Vector for Expression of Mimetic Peptide of Apolipoprotein B100

Step 1: Design of the Vector

The plasmid vector for expression of mimetic peptide generally comprises a leader cassette and one or more PB1 peptide gene. As depicted in FIG. 1, the plasmid pBX1 which comprises one (1) PB1 gene was prepared by cloning the leader cassette (FIG. 1A) at the multiple cloning site of pQE30 plasmid (Qiagen, Hilden, Germany). The resulting plasmid was digested with HindIII and SalI and the small fragment was replaced by the LB cassette (FIG. 1B) to give the plasmid pBX1 which is good for the insertion of multiple numbers of BL cassettes (FIG. 1C) easily.

Meanwhile, the plasmid pBluescriptH SK+ was cut with SalI and XhoI and ligated with BL cassettes in which single to multiple BL cassette insertions occurred randomly. The expected repeats of the PB1 peptide genes in the plasmid pBlue-BL were selected and cleaved out and subcloned into pBX1 (FIG. 1D).

Step 2: Preparation of Vector for Expression of PB1 Mono-peptide

A leader cassette was prepared by annealing SEQ ID NO:10 and SEQ ID NO:11 oligonucleotides synthesized through the same process as Example 1 and 2. Then, the pQE30 vector (Qiagen, Hilden, Germany), which had been cleaved by SalI and BamHI, was ligated with the above leader cassette in order to prepare pQE-Leader plasmid. As a result of expression of the above pQE30 vector, six histidine residues were additionally incorporated to the N-terminus of the expressed protein in order for the protein to be purified easily. The above leader cassette was designed to comprise a recognition site (DDDDKI; SEQ ID NO:12) for enterokinase in order to reduce the additional amino acids to a minimum.

According to the process of Example 1, four oligonucleotides of the sequences of which are represented by SEQ ID NOS:4 to 7, were synthesized, phosphorylated, and then, annealed with complementary oligonucleotides respectively in order to synthesize the LB cassette of FIG. 1B (SEQ ID NOS:13 and 14). 40 $\mu$L of the annealed oligonucleotides were mixed with 3 $\mu$L of 1 U/$\mu$L T4 DNA ligase, 5 $\mu$L of 10×enzyme buffer and 2 $\mu$L $\mu$L of distilled water to prepare ligation mixture. Then, the ligation mixture was incubated overnight to link the oligonucleotides each other.

After the reaction was completed, the reaction mixture was loaded onto 20% polyacrylamide gel and electrophoresed. The LB cassette (52 bp oligonucleotides) (FIG. 3) was identified by dying the gel with ethidium bromide (EtBr).

In FIG. 3, lane M was a mark for 20 bp ladder DNA, and lane 1 was the reaction solution. LB cassette was obtained from the gel by means of QIAEX II gel extraction kit (Qiagen, Hilden, Germany).

The above pQE-Leader was cleaved by HindIII and SalI, and then ligated with the above LB cassette according to Example 2 in order to prepare expression vector for PB1 mimetic peptide. The prepared expression vector was named pBX1 and the peptide expressed by the vector was named PB11 peptide (refers to FIG. 2).

Step 3: Preparation of Expression Vector for PB1i Peptide Concatemer

According to the process of Example 1, four oligonucleotides the sequences of which are shown in SEQ ID NOS:4, 5, 8, and 9, were synthesized, phosphorylated and then, annealed with complementary oligonucleotides respectively in order to synthesize BL cassette of FIG. 1C (SEQ ID NOS:15 and 16). Subsequently such oligonucletides were ligated with each other like the process of Step 2 and then were loaded onto 20% polyacrylamide gel for electrophoresis. Fifty-five bp oligonucleotide (leader cassette) was identified by staining the gel with EtBr. BL cassette was obtained from the gel through QIAEX II gel extraction kit and cleaved by SalI and XhoI.

Meanwhile, a pBluescript II SK (Stratagene, La Jolla, Calif., USA) was cleaved by SalI and XhoI. The vector was electrophoresed on 0.8% agarose gel, and obtained by means of QIAEX II gel extraction kit (Qiagen, Hilden, Germany).

The same ligation reaction as Example 2 was carried out to obtain pBlue-BL plasmid by using 5 of BL cassette DNA and 1 of the above cleaved-vector DNA.

Figure 2:
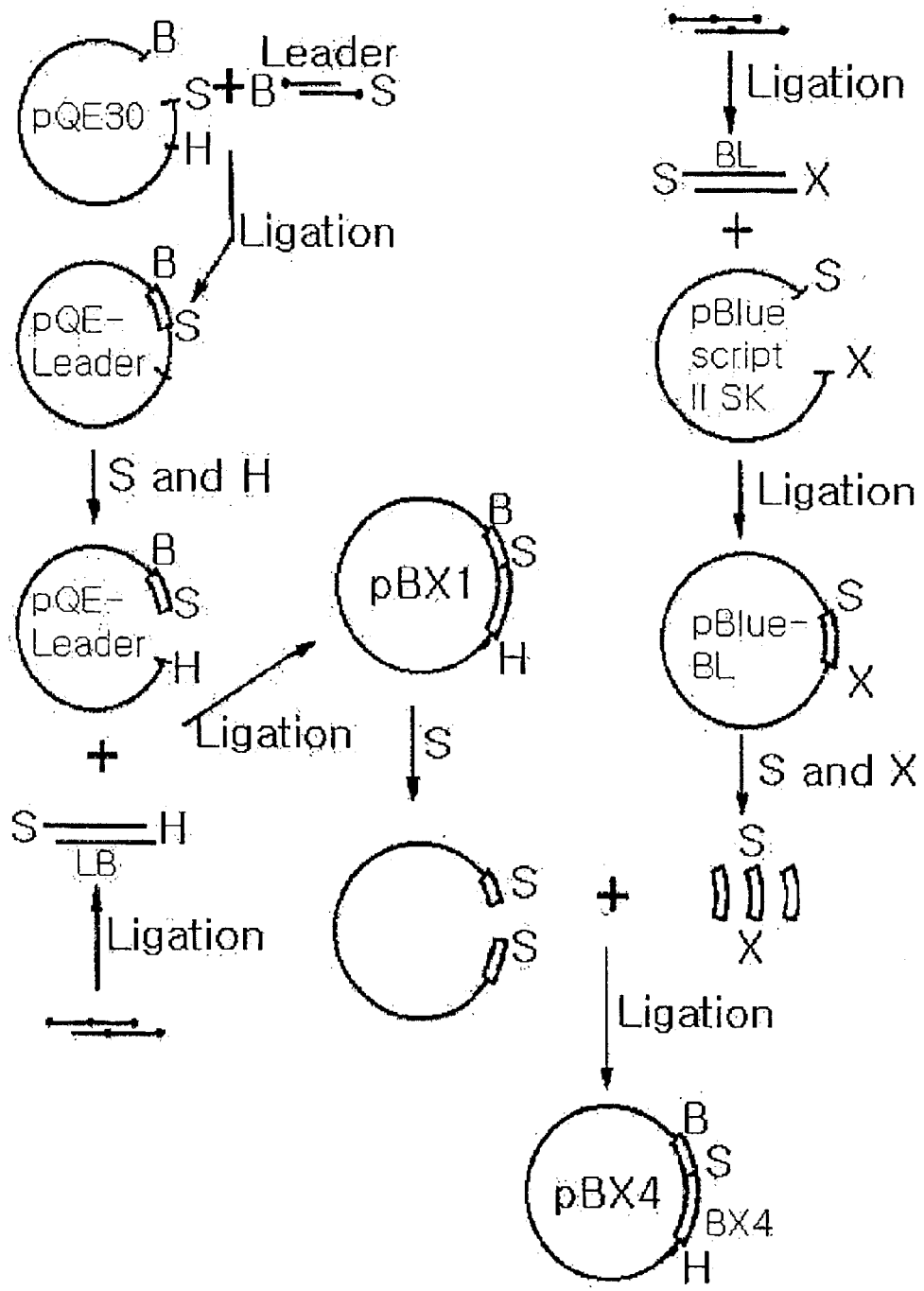
FIG. 2 represents the procedures for preparation of pBX1 and pBX4 vector for expressing the mimetic peptide of the present invention.
Figure 3:
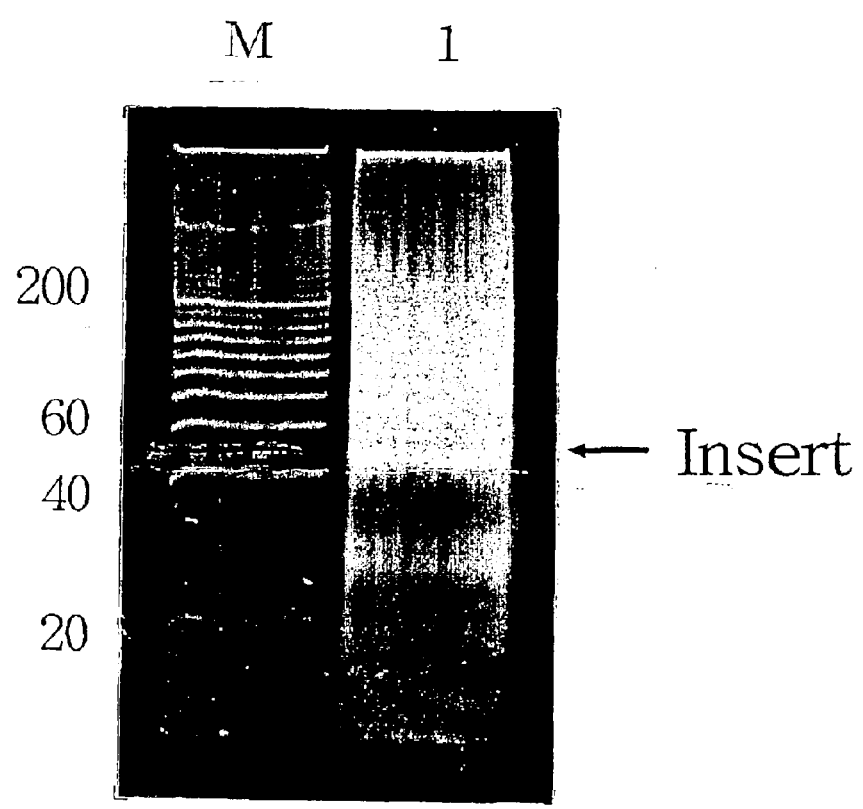
FIG. 3 represents the result of polyacrylamide gel electrophoresis (PAGE) for the identification of LB cassette.

The pBlue-BL was cleaved by SalI and XhoI, and the BL cassette was extracted. Plasmid pBX2 was prepared by inserting such BL cassette into the SalI site of the pBX1 vector prepared in Step 2. In addition, pBX3 and pBX4 vector were prepared by changing the number of the BL cassette which inserted into the SalI site of the pBX1 vector from two (2) to three (3) (refers to FIG. 2).

The peptides expressed from the pBX2, pBX3 and pBX4 vector, were concatemers which comprises two (2) to four (4) PB1 peptides. They were named PB12, PB13 and $PB1_4$ respectively.

Step 4: Identification of the Insert

Figure 4:
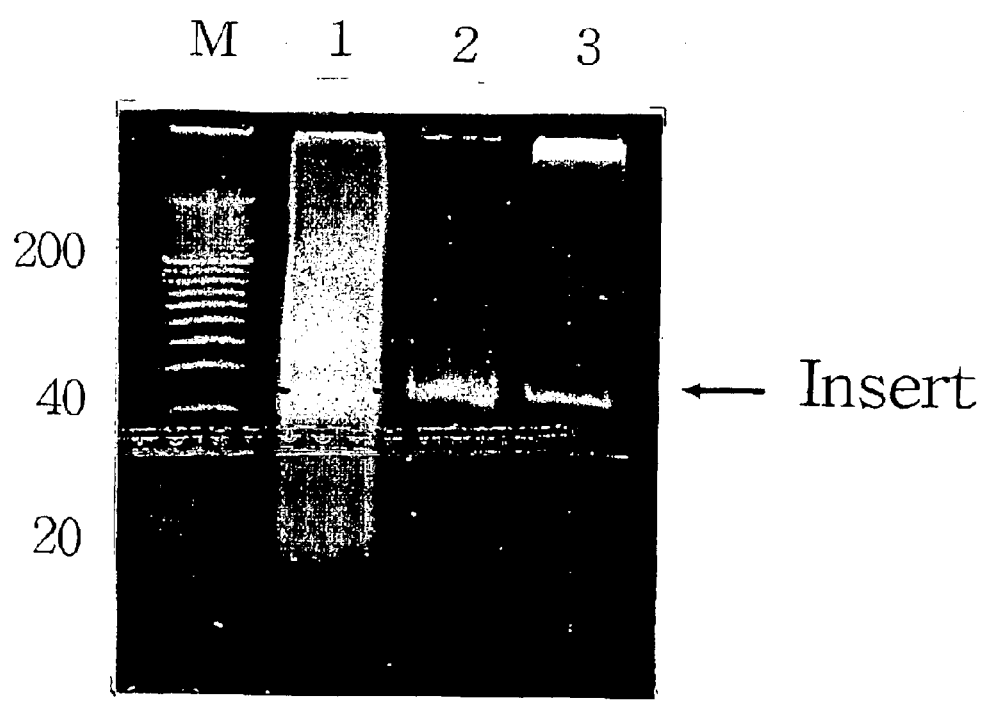
FIG. 4 represents the result of PAGE for the identification BL cassette incorporated in plasmid pBlue-BL.

Host cells (*E. coli* M15 [pREP4]; Qiagen, Hilden, Germany) were transformed with the pBlue-BL plasmid, spread onto 1% agar plate, and then incubated for 16 hours at 37° C. so that colonies of *E. coli* could be formed. One of the colonies that formed on the agar plate was inoculated in 10 mL of LB medium and incubated with shaking at 37° C. for sixteen (16) hours, and then the plasmid was isolated through DNA purification system (Wizard PLUS SV DNA miniprep DNA purification system; Promega, Madison, Wis., USA). The plasmid harvested from the transformed *E. coli* was incubated with SalI and XhoI restriction enzyme in order to be cleaved at 37° C. for one (1) hour, and analyzed through 20% PAGE (FIG. 4). In FIG. 4, lane M represents 20 bp ladder DNA, lane 1 represents oligonucleotide product obtained from Step 3, lane 2 represents BL cassette DNA isolated by 20% PAGE from step3 and lane 3 represents recombinant pBlue-BL plasmid treated with restriction enzyme. As shown in FIG. 4, it was confirmed that the pBlue-BL plasmid contained BL cassette.

Figure 5:
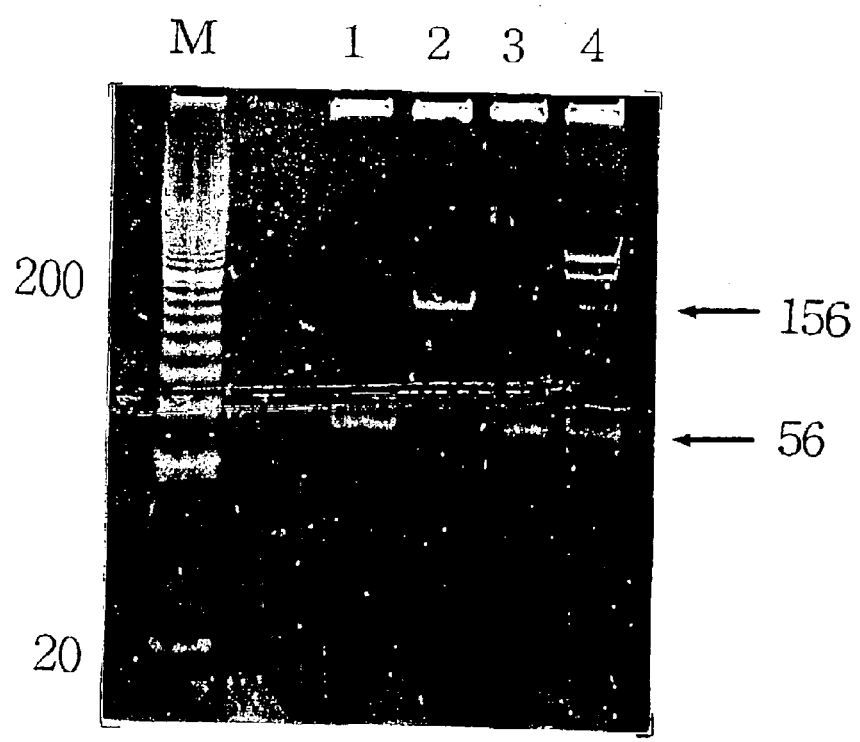
FIG. 5 represents the result of PAGE for the confirmation of the direction and the number of copy of DNA inserted in plasmid pBX1 and pBX3.

*E. coli* (M15 [pREP4]) was transformed with pBX1 or pBX3 plasmid and plasmid DNA was isolated as explained above in order to confirm the number and orientation of the DNA cassette inserts. The isolated plasmid was cleaved by SalI and HindIII restriction enzyme and analyzed through 20% PAGE (FIG. 5). In FIG. 5, lane M represents 20 bp ladder DNA; lanes 1 and 3 represent the pBX1 plasmid containing an LB, but not BL cassette; and lane 2 represents the plasmid harboring one LB and two BL cassettes with the right direction. On the other hand, lane 4 represents the plasmid having one LB and two BL cassettes with reversed orientation. As shown in FIG. 5, the number and orientation of B cassettes (BL or LB cassette) were determined by restriction enzyme mapping.

In addition, the DNA sequence of the B cassettes incorporated into the plasmid which had been harvested from the transformed *E. coli*, was confirmed to be identical to the designed sequences. The plasmids were prepared by Wizard PLUS DNA miniprep kit and were sequenced by using Sequennase (Ver. 2.1) DNA sequencing kit (Amersham, Cleveland, UK).

EXAMPLE 4

Expression of $PB1_4$ Peptide in *E. coli* and its Purification

Step 1: Confirmation of Expression of $PB1_4$ Peptide

To confirm the expression of $PB1_4$ peptide, three kinds of transformed *E. coli* M15 [pREP4] were cultivated on LB agar broth containing ampicillin and kanamycin. One *E. coli* M15 [pREP4] was transformed with the plasmid pBX4, another was mock transformed with pQE30, and the other was not transformed *E. coli* M15 [pREP4]. Each of colonies formed from the solid culture was inoculated respectively in liquid LB culture medium which contained 100 μL/mL ampicillin and 25 μL/mL kanamycin, and incubated overnight. The culture was incubated at 37° C. for one (1) hour with shaking until the O.D. value reached 0.5 to 0.7 at 600 nm. Thereafter, 1 mM isopropyl-thio-β-galactopyranoside (IPTG) was added to the culture medium to facilitate the expression of the recombinant protein, and additional cultivation was made at 37° C. for five (5) hours. 1 μL of the culture medium was centrifuged at 14,000 rpm for two (2) min to precipitate the bacterial cells. The cell pellet was suspended in 50 μL of 2×SDS solution [100 mM Tris-Cl pH 6.8, 20% glycerol (w/v), 4% SDS (w/v), 2% 2-mercaptoethanol, 0.001% bromophenol blue] to apply in SDS-PAGE. The suspended solution was heated at 95° C. for five (5) min, and then 10 μL of the solution was loaded in the well of the casted gel and electrophoresed at 20 mA for five (5) hours (Mighty Small II, Hoefer, USA). Acrylamide concentrations of the stacking gel and resolution gel which were employed, were 5% and 15% respectively, and pre-stained standard SeeBlue (250 kDa to 4 kDa; NOVEX, San Diego, Calif., USA) or wide-ranging standard Mark12 (200 kDa to 2.5 kDa) were used as a standard size marker protein. After electrophoresis, the gel was stained with Coomassie brilliant blue R-250 for one (1) hour and dyed destained with decolorizing solution (5% Methanol and 7% acetic acid) for ten (10) hours.

Figure 6:
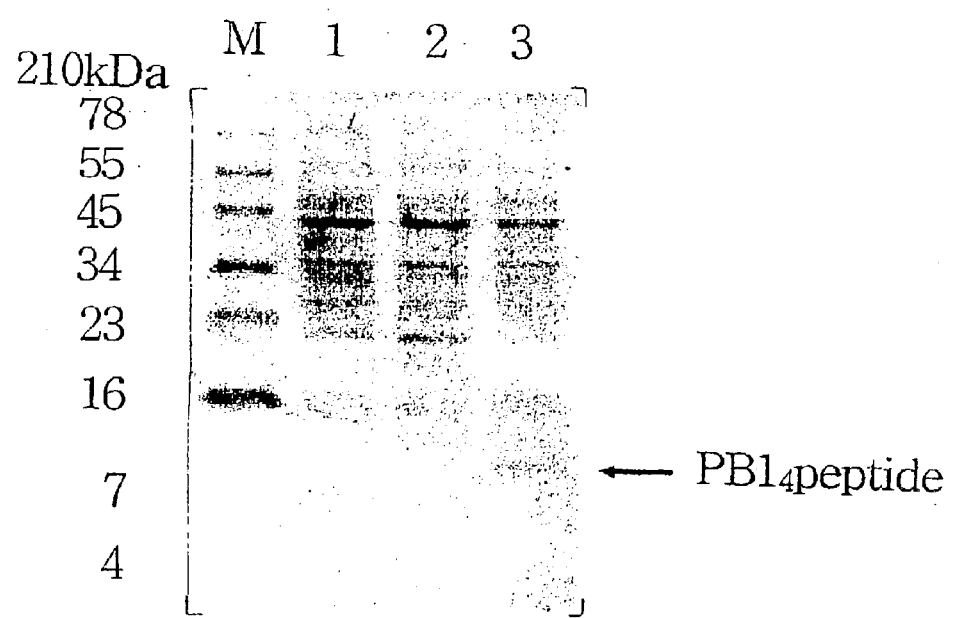
FIG. 6 represents the result of western-blotting for identification of the expressed $PB1_4$ peptide.

To confirm that the expressed protein is $PB1_4$ peptide, the proteins in the electrophoresis gel, western-blotting was carried out using anti-PB1 rabbit antibody (FIG. 6). Antiserum was produced by immunizing ovalbumin conjugated which was PB1 peptide chemically synthesized by Bio-Synthesis, Inc. (Lewisville, Tex., USA). In FIG. 6, lane M represents the pre-stained standard SeeBlue label, lane 1 represents medium used for incubation of *E. coli* M15 [pREP4] which was not transformed, lane 2 represents medium used for incubation of *E. coli* M15 [pREP4] which was transformed with pQE30 vector, lane 3 represents medium used for incubation of *E. coli* M15 [pREP4] which was transformed with pBX4 vector.

As depicted in FIG. 6, only the pBX4 transformed *E. coli* expressed the recombinant $PB1_4$ peptide represented a specific immunity with anti-PB1 mouse serum.

Step 2: Identification of Solubility of the Expressed Peptide

*E. coli* M15 [pREP4] which had been transformed with pBX4 vector, was incubated as the same method of Step 1. 10 mL of the culture medium was taken and centrifuged to harvest the cells. The cell pellet was suspended in 5 mL of cell lysis solution (300 mM NaCl, 50 mM $NaH_2PO_4$, 10 mM imidazol pH 8.0) to obtain natural protein from the cell. After being chilled, the pellet-suspended solution was sonicated 20 cycles with ultrasonic wave in order to lyse the cells. The supernatant was taken by centrifuge at 4° C., 10,000 rpm for 30 min. The same volume of 2×SDS solution was mixed with solution and SDS-PAGE was carried out as the same method described in Step 1. After boiling each solution at 95° C. for 5 min As a result of SDS PAGE, it was confirmed that $PB1_4$ peptide could be isolated and purified from the soluble extract A in that it was contained in the insoluble crude extract B.

Step 3: Purification of $PB1_4$ Peptide

Step 3-1: Affinity Chromatography

Ni-NTA resin for purifying His-tagged proteins, was used to purify the recombinant peptide in Step 1. The affinity chromatography using attractive force between Ni+ saturated in resin and histidine residues at the end of the expressed protein, is a well known method for purifying interest protein easily.

First of all, E. coli M15 [pREP4] which had been transformed with pBX4, was inoculated in 1l of LB culture medium and incubated at 37° C. to the extent that O.D. value was over 0.6 at 600 nm. The ratio of LB culture medium to pBX4 vector was fifty (50) to one (1). IPTG was added in a final concentration of 1 mM and incubated again for five (5) hours. After incubation, the cell pellet was obtained by centrifuging the culture medium at 6,000×g for 30 min, and the pellet was stored at −70° C. over night. The pellet was thawed in ice, suspended in dissolving solution (300 mM NaCl, 50 mM $NaH_2PO_4$, 10 mM imidazol pH 8.0) wherein 5 mL of dissolving solution per 1 g of the pellet was used. Cells are lysed by sonication as the method of Step 2 and then centrifuged at room temperature at 10,000×g for 30 min. The same volume of buffer (8 M urea, 0.1 M $NaH_2PO_4$, 0.01 M Tris-HCl pH 8.0) as the pellet, was added for re-suspending the cellular debris and for denaturing proteins there in, and the pellet-suspended solution was treated with brief ultrasonic wave so that more proteins could be dissolved in buffer. The suspension was centrifuged at 8,000 rpm for 30 min to remove cellular debris which had not been solubilized in 8M urea. To the 4 mL of the supernatant above, 1 mL of Ni-NTA resin was added at 4° C. and shook 200 rpm for 2 hours in order proteins containing His-tag to be captured.

Figure 7:
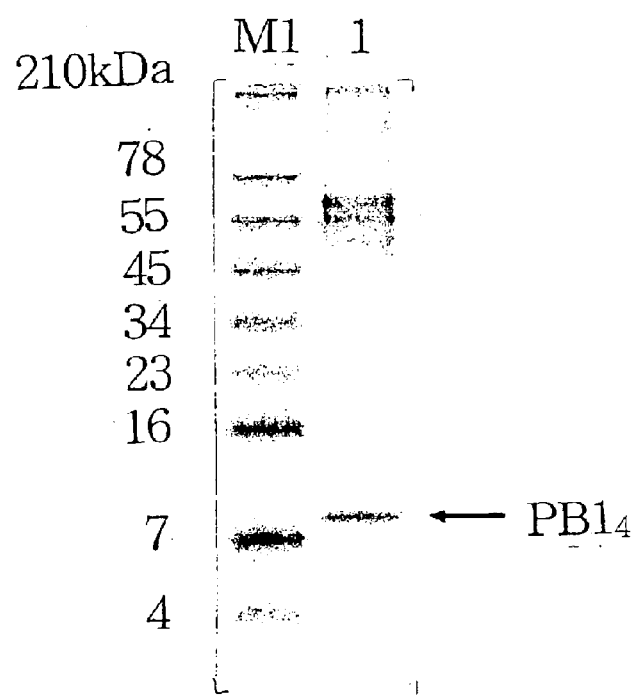
FIG. 7 represents the result of sodium dodecyl sulfate (SDS) PAGE for confirmation of the purified $PB1_4$ peptide.

Such supernatant containing protein/Ni-NTA complex was poured carefully into the chromatography column (size 2 cm (id)×2.7 cm (h)). Excess buffer was drained by opening the cap after the resin had been sunk down. The column was washed with 20 mL of medium pH buffer (8 M urea, 0.1 M $NaH_2PO_4$ 0.01 M Tris-HCl pH 8.0) and subsequently 20 mL of another buffer (8 M urea, 0.1 M $NaH_2PO_4$ 0.01 M Tris-HCl pH 6.3) in order to wash out proteins which had been non-specifically bound to the Ni-NTA resin. The target proteins containing His-tag were eluted by pouring 5 mL of low pH buffer (8 M urea, 0.1 M $NaH_2PO_4$ 0.01 M Tris-HCl pH 5.9) two (2) times and subsequently 5 mL of strong acid buffer (8 M urea, 0.1 M $NaH_2PO_4$, 0.01 M Tris-HCl pH 4.5) four (4) times, and then SDS-PAGE was used to confirm the eluted target proteins by using 15% acryamide gel (FIG. 7). In FIG. 7, lane M represents pre-stained SeeBlue size marker and lane 1 represents the purified $PB1_4$ peptide.

The above purified proteins are dialyzed against PBS (8 g/L NaCl, 0.2 g/L KCl, 1.44 g/L $Na_2HPO_4$ and 0.24 g/L $KH_2PO_4$) in order to regain their original conformations. Dialysis tube employed, was 3,500 Da in molecular weight cut-off size. During dialysis, 3L of PBS containing 2 M urea was used first for 5 hours, and then 5 L of PBS without urea was used two (2) times overnight.

Step 3-2: Hydrophobic Chromatography

Hydrophobic chromatography was carried out in order to improve the purity of the $PB1_4$ peptide which had been obtained in Step 3-1.

Ammonium sulfate was added up to final 20% concentration little by little to the solution containing $PB1_4$ peptide, which was eluted from Ni-NTA resin in Step 3-1, and then adjusted to pH 7.0. The solution was left for three or more hours after 10% of ammonium sulfate had been melt completely, and then the solution was loaded on the phenyl sepharose column [a filling: Phenyl sepharose Fast Flow resin (Phamacia, Sweden); column size: 1 cm (id)×3 cm (h)].

Each fraction which was eluted from the column by pouring eluting solution (8 M urea, 0.1 M $NaH_2PO_4$, 0.01 M Tris-HCl pH 6.3) into the column at the flow rate of 0.5 mL/min under the reverse gradient of ammonium sulfate from 10% to 0%, was loaded on the gel for SDS PAGE. The fraction containing $PB1_4$ peptide was collected and dialyzed in a buffer solution to be desalted, and urea which had been used as a denaturating agent, was removed at the same time.

Step 3-3: Removal of His-tag

2 M urea was added to buffer solution (50 mM NaCl, 20 mM Tris-HCl, 2 mM $CaCl_2$ pH 7.4) which was good for removing denaturating agent and imidazol etc. from the purified his-tagged protein and also for activating enterokinase. The dialyzed $PB1_4$ peptide which had been obtained from Step 3-2, was dialyzed again by using the above urea containing buffer to desalt the $PB1_4$ peptide, and during which, the concentration of urea was lowered little by little by repeated dialysis against urea depleted buffer. 3 U/ml of enterokinase was added to the $PB1_4$ peptide-containing solution of which buffer was changed with the said second buffer, and incubated at 23° C. The solution which was taken at every hour, then was analyzed by SDS-PAGE in order to check the amount of his-tag removal from the his-tagged PB1 ($PB1_4^{+his}$) peptide.

Step 3-4: Ion Exchange Chromatography

Unwanted proteins and peptides which had been produced as a result of treatment of enterokinase, were removed through ion exchange chromatography.

The solution containing $PB1_4^{-his}$ peptide which had been obtained in Step 3-3, was dialyzed in dialysis buffer (2 M urea, 0.1 M $NaH_2PO_4$, 0.01M Tris-HCl, pH 7.0), and the buffer was exchanged sufficiently. The solution which had been dialyzed, was loaded on the DEAE sepharose resin (Phamacia, Uppsala, Sweden). Thereafter, the column was equilibrated with equilibrating buffer (50 mM sodium phosphate buffer, 2 M urea, pH 7.0) and the peptide was eluted under NaCl concentration gradient from 0 to 1M by using another buffer (50 mM sodium phosphate buffer, 2 M urea, 1 M NaCl) (flow rate: 0.5 mL/min). Each fraction was recovered and target protein containing fraction were pooled. The presence of $PB1_4^{-his}$ peptide was confirmed through SDS-PAGE after concentrating the compartments.

Step 4: Quantitative Analysis of $PB1_4$

The purified $PB1_4$ peptide which had been obtained through the same method of Step 3, was quantitatively analyzed through colorimetric analysis by using micro BCA reagent (Pierce, Rockford, USA).

Step 5: Confirmation of Characteristics of the Recombinant $PB1_4$ Peptide

Purity of the $PB1_4$ peptides which had been purified in Step 3 and immunogenicity of them against anti-serum which had been obtained by using synthetic $PB1_4$ peptide as a antigen, were confirmed through western-blot assay by ECL (Amersham, Cleveland, UK). After SDS-PAGE (Example 2, Step 1), the gel was incubated together with PVDF membrane in buffer (0.3% Tris, 1.5% glycine, 20% methanol) at a constant voltage of 60V for three (3) hours in order for the protein in the gel to be transferred into the PVDF membrane. Then, the blotted membrane was incubated with a 5 mL of blocking solution (TBS pH 7.5, 5% skim milk powder (w/v), 0.02% Tween 20) for 1.5 hours, and then was washed three times with TTBS (Tris-buffered saline solution containing 0.1% Tween 20) for 15 min, 5 min and 5 min respectively. The antiserum against the peptide PB1 (refers to Step 1 of Example 2) was diluted with the TTBS solution in ratio of one (1) to five thousand (5,000), and then incubated with the membrane for 1.5 hours. To confirm the purity of the $PB1_4$ peptide, anti-serum against PB1$_4$ peptide (Example 3). After washing the gel with TTBS three times for 15 min, 5 min and 5 min in turn, the membrane was incubated for 1.5 hours at room temperature with the solution in which alkaline phosphatase-F(ab)'2-goat anti-mouse IgG (H+L) (Zymed, San Francisco, Calif.) was diluted with the TTBS solution in ratio of one (1) to one thousand (1000). The membrane was washed again with TTBS three times, and then colorized by adding BCIP/NBT (5-bromo-4-chloro-3-indolyl phosphate/nitro blue tetrazolium (Sigma)). BCIP/NBT solution was removed using TTBS solution after staining. As a result of western-blotting analysis, the expressed PB1$_4$ peptide could be recognized with the anti-PB1$_4$ serum.

Figure 8:
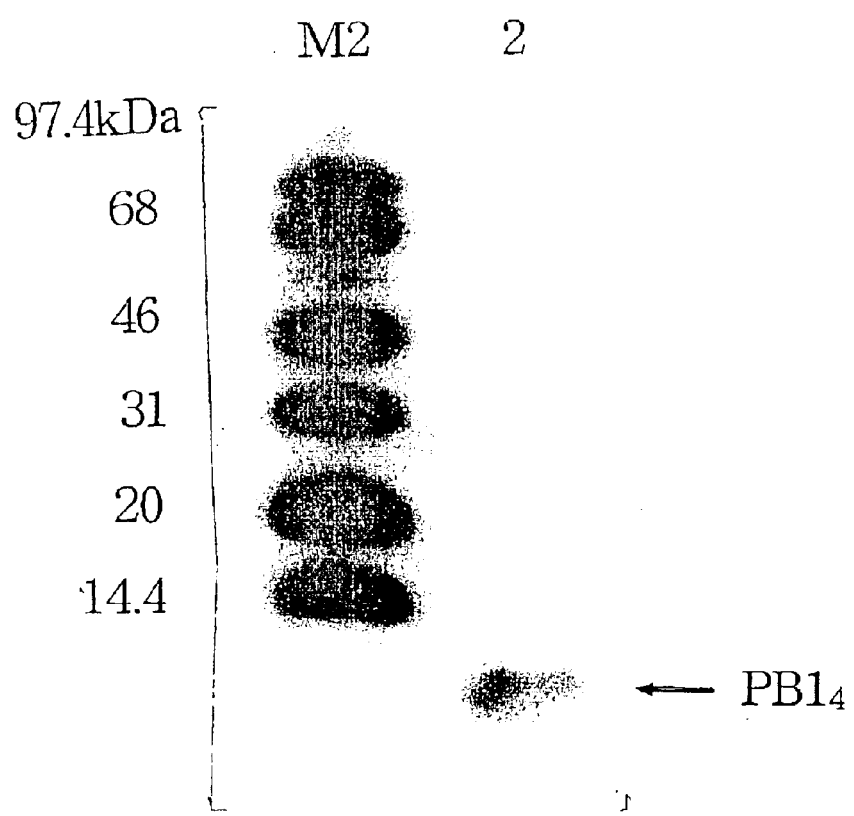
FIG. 8 represents the result of western-blotting for confirmation of the reactivity of the purified $PB1_4$ peptide against anti-$PB1_4$ serum.

In case of ECL, PVDF membrane (Gelman Science, BioTrace®) was used instead of nitrocellulose membrane. In addition, the first antibody was used in ratio of one (1) to ten thousand (10,000) and HRP-conjugated rabbit anti-mouse IgG (Pierce, Rockford, Ill., USA.) was used as the second antibody in ratio of one (1) to ten thousand (10,000). 1 mL of solution A of ECL+Plus western-blot agent (Amersham) per 25 ml of solution B, was used in color reaction. When color was generated sufficiently, the membrane was inserted into film cassette for 5, 10, 20 and 30 seconds respectively to be exposed to the film so that the bands on the gel could be detected (FIG. 8). In FIG. 8, lane M represents a ECL detecting label (Gibco BRL) and lane 1 represents the PB1$_4$ peptide. As the result from FIG. 8, the expressed PB1$_4$ peptide could be recognized with the anti-PB1$_4$ serum.

In addition, the result of western-blot analysis on which the PB1$_4$ peptide using polyclonal antibody isolated from rabbit serum by using Protein G column (Bio-Rad, USA), gave the same result.

EXAMPLE 5

Preparation of Anti-PB1$_4$ Peptide Mouse Antibody

The PB1$_4$ peptide used herein was the PB1$_4^{-his}$ peptide from which his-tag was removed, in step 3-3 of example 2.

Step 1: Ligation Between PB1$_4$ Peptide and OVA

As a carrier protein, ovalbumin (OVA), was added to the purified PB1$_4$ peptide in Step 3 in Example 2, in molar ration of one (1) to ten (10), and was incubated for one (1) hour at 4° C. To the PB1$_4$ peptide-ovalbumin solution, 2% (v/v) glutaraldehyde was added with the same volume, and incubated for one (1) hour with continuous shaking. Then glycine was added to the reaction mixture until final concentration is to be 0.2 M to stop the reaction proceeding therein.

After the reaction, the remaining glutaraldehyde and glycine in reaction mixture, were removed by dialysis using MWCO 12,000–14,000 dialysis membrane (Spectrum®, Dominguez, Calif., USA).

Step 2. Immunization of Mouse

The peptide with which OVA was linked in Step 1 was concentrated and used to immunize mouse. The amount of the antigen to be injected to the mouse was 5 µg, which was the amount of PB1$_4$ peptide before linked with OVA. The antigen which was emulsified with the same amount of an adjuvant, was injected to intraperitoneum cavity of the mouse in amount of 0.2 mL.

Complete Freund's Adjuvant (CFA) was used as the adjuvant of the first injection, and Incomplete Freund's Adjuvant (IFA) was used as the adjuvant at the boosting immunization for two (2) times by two (2) weeks interval. In control mouse, BSA (bovine serum albumin) was injected.

After five (5) days from the final injection, 1 mL of blood was taken from mouse by cardiac puncture and the blood was clotted for 30 min at 37° C. Then, the blood was centrifuged for 30 min at 4° C., 2500×g and the clot was removed from the blood. The supernatant (i.e., blood serum) was incubated overnight at 4° C. for the remaining blood coagulants to be concentrated completely, and centrifuged for 20 min at 10,000×g. The resulting supernatant was aliquoted into several tubes. The blood serum which was to be used in experiment, was stored at 4° C., and the remainders were stored at −20° C.

Step 3. Measurement of Avidity of Anti-PB1$_4$ Antibody by Indirect ELISA

Figure 9:
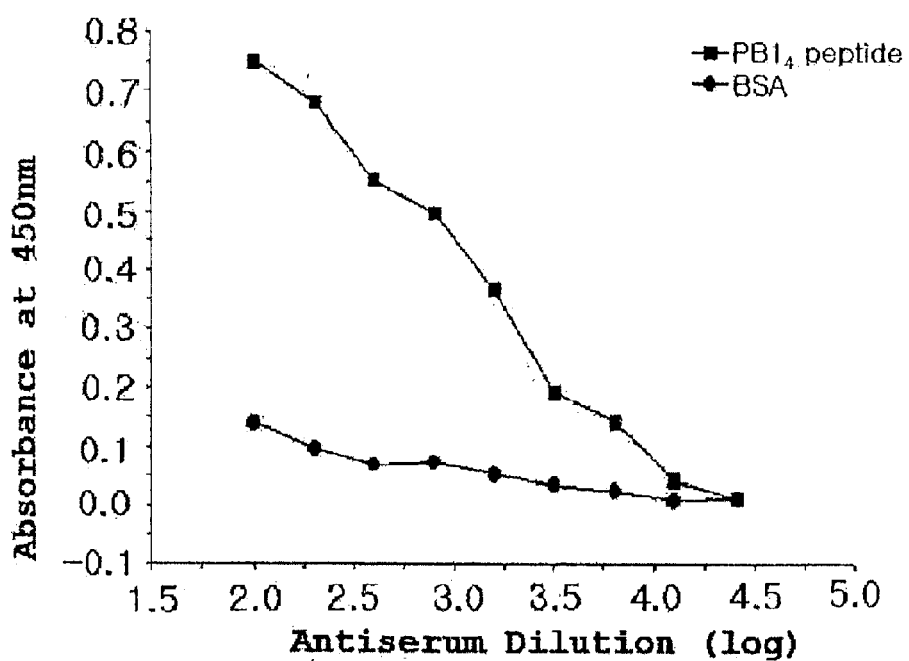
FIG. 9 represents the result of ELISA for measurement of the avidity of the antibody of mouse induced by $PB1_4$ peptide.

The avidity of the antibody was measured by using blood serum obtained in Step 2. 100 µL of PB1$_4$ peptide was distributed into each well of 96 well of a micro-titer plate (Flacon: pro-binding), left alone at 4° C. for 6 hours or more, and then washed three (3) times with TTBS (Tris bufferedsaline solution containing 0.05% Tween 20). 200 µL of blocking solution (1% BSA in TTBS) was added to each well and incubated at 37° C. for one (1) hour, and then washed three (3) times with TTBS. 100 µL of the isolated serum which had been diluted with the blocking solution in ratio of one (1) from 102 to 105, was added to the reaction solution and incubated at 37° C. for 1 hour, and then washed three (3) times with 200 µL of TTBS. 100 µL of HRP-linked goat anti-rabbit IgG antibody (Pierce, Rockford, Ill.), which had been diluted with the blocking solution in ratio of one (1) to 103, was added to the reaction solution and incubated at 37° C. for 1 hour, and washed three (3) times with 200 µL of TTBS. Solution A of the HRP substrate kit (Bio-Rad) was mixed with solution B of the same in ratio of nine (9) to one (1). 100 µL of the resultant mixture was added to the reaction solution and colorized for thirty (30) min, and then optical absorbency for the reaction mixture was measured at 405 nm by using ELISA leader (EL312e, Bio-Tek Ins.) (FIG. 9). In FIG. 9 it was confirmed that the mouse antibody specific for PB1$_4$ peptide could be applied to western-blot and ELISA analysis by one (1) thousand fold (3.0 of the X axis in figure).

EXAMPLE 6

Anti-Obesity Effect of PB1$_4$ Vaccine by Using a Mouse Model

Step 1: Induction of Obesity in a Mouse 5 week-old ICR mice (Korea Center for Animal Experiment Ltd., Seoul, Korea) were used herein. The mice were raised in a breeding farm in which the temperature was from 17° C. to 25° C., and were fed a mixed feed (Sam Yang Feed Ltd., Seoul, Korea, [ingredient: water 11.8% or more, protein 20.0% or more, crude lipid 3.0% or more, crude fiber 10.0% or less, crude ash 10.0% or less, calcium 0.6% or less and phosphorus 0.4% or more]). Goldthioglucose (GTG) was administered to the mice to induce obesity. GTG has a role of inducing desensitization of venteromedial hypothalamic nuclei (VMH). Therefore, the mice that received GTG did not feel satiated and always had a desire to eat. The GTG used herein is very unstable since it is easily degraded in water or moisture. Therefore, 100 mg of GTG (Sigma, Inc.) was diluted with 1 mL of sesame oil (Sigma Inc.), and was used as the same method of Brecher et al (Brechere G. and Waxler, S. H. Proc. Soc. Exp. Biol. Med., 70: 498501 (1949)) in order for a proper amount of GTG to be administered.

The mice were distributed to prepare a test (twenty (20) mice) and a control group (four (4) mice), and 25 mL of GTG was injected to the test group whereas the control was injected with nothing.

Body weight of the mice of the test group was measured prior to experiment and the mice of which deviation of body weight was not significant, were selected and applied to experiment. Body weight of the mice measured after one (1) week after GTG injection, was in the range from 26.5 to 29.5 grams.

Seven mice of the GTG-injected group were induced to be obese whereas the remainder was not. The mice which were not induced to be obese, was injected again with GTG, then all the mice were induced to be obese.

All of the obesity-induced mice were distributed in three (3) groups. A week later from second GTG injection the $PB1_4$ peptide was injected to the mice of test group 1 consisting of seven (7) mice as the same method in Step 2 of Example 3. In addition, the mice (test group 2 containing seven (7) mice) of another group of the three, were injected with ovalbumin instead of $PB1_4$ peptide as a mock experiment, and vaccine was not injected to the other group (test group 3 containing six (6) mice) to induce obesity. On the other hand, 0.2 mL of PBS was injected to the control group to be compared with the test groups to confirm the effect of the vaccine of the present invention.

In addition, feed used herein was mixed with the yolk of an egg and dried at 50° C. to induce intake of cholesterol so that the level of cholesterol could increase in mouse serum. Feed was also provided enough for disease related to the level of cholesterol to be caused. Body weight of the mouse was measured everyday.

Figure 10:
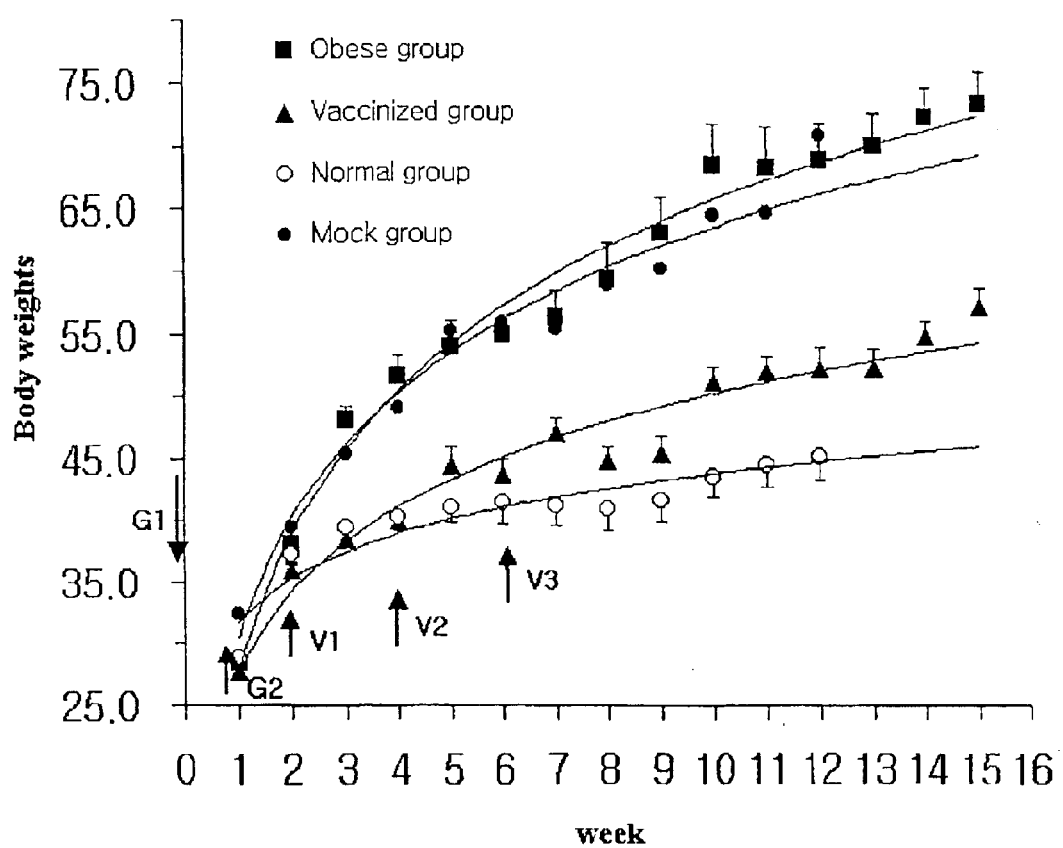
FIG. 10 is illustrates the suppressing effect of $PB1_4$ on the increase of body weight of mouse.

As depicted in FIG. 10, body weight of the vaccine-injected mice of test group 1 (-▲-▲-) increased from 27.7±0.4 g to 52.2±1.7 g after twelve weeks (12) of GTG injection. The data justify a conclusion that there was no significant difference of an increase in body weight between the test group 1 and the control group (-○-○-). However, body weight of the mice of both the test group 2 (-●-●-) in which ovalbumin was injected after being obese and the test group (-■-■-) in which no vaccine was injected after the induction of obesity, increased continuously from 28.3±0.5 g to 68.9±2.8 g. Therefore, it was confirmed that obesity could be inhibited by injection of $PB1_4$ peptide vaccine.

In FIG. 10, G1 and G2 represent the time of GTG injection and V1, V2 and V3 represent the time of injection of $PB1_4$ peptide vaccine.

Figure 11A:
FIGS. 11A and 11B illustrate the change in body weight of mice depends on administration of $PB1_4$ vaccine of the present invention 20 weeks after injection of a drug which can destroy of hypothalamus.
Figure 11B:

FIG. 11 represents appearance of the obesity-induced mice. A 20-week old mouse of the test group 1 (FIG. 11A: normal mouse) was compared with a 20-week old mouse of the test group 3 (FIG. 11B: obese mouse). As depicted in FIG. 11, it was confirmed that the vaccine of the present invention was effective in inhibiting obesity.

Step 2: Measurement of the Level of Cholesterol in Blood.

After the first GIG injection, blood cholesterol level of 12-week old mouse of the control group was compared with that of 12-week old GTG-injected mouse of the test group 1, 2, and 3. Concentration of total cholesterol, triglyceride, 1-IDL-cholesterol and LDL-cholesterol was measured through an enzymatic method by using Cholestezyme-V, Triglyzyme-V, HDL-C555 (Shin Yang Chemicals, Seoul, Korea) and LDL-EX kit (Denka Bio-Research, Ltd., Tokyo, Japan). In each experiment, a standard curve for O.D. value was prepared by using standard Calibrater-D (Denka Bio-Research, Ltd., Tokyo, Japan) to decrease an experimental error. The O.D. value for the interest was calculated based on the calibration curve to confirm the concentration and content of the lipid, the result was depicted in Table 1 and FIG. 12.

TABLE 1

|  | Total cholesterol | TG | HDL-C | |
| --- | --- | --- | --- | --- |
| Control | 79 ± 3.7 | 180 ± 26 | 59 ± 3.4 | |
| Test group 1 | 118 ± 3.6 | 217 ± 47 | 92 ± 4.7 | 20 ± 1.7 |
| Test group 2 and 3 | 131 ± 8.8 | 218 ± 70 | 119 ± 7.5 | 30 ± 4.5 |

TG: triglyceride, HDL-C: HDL-cholesterol, LDL-C: LDL-cholesterol

Figure 12:
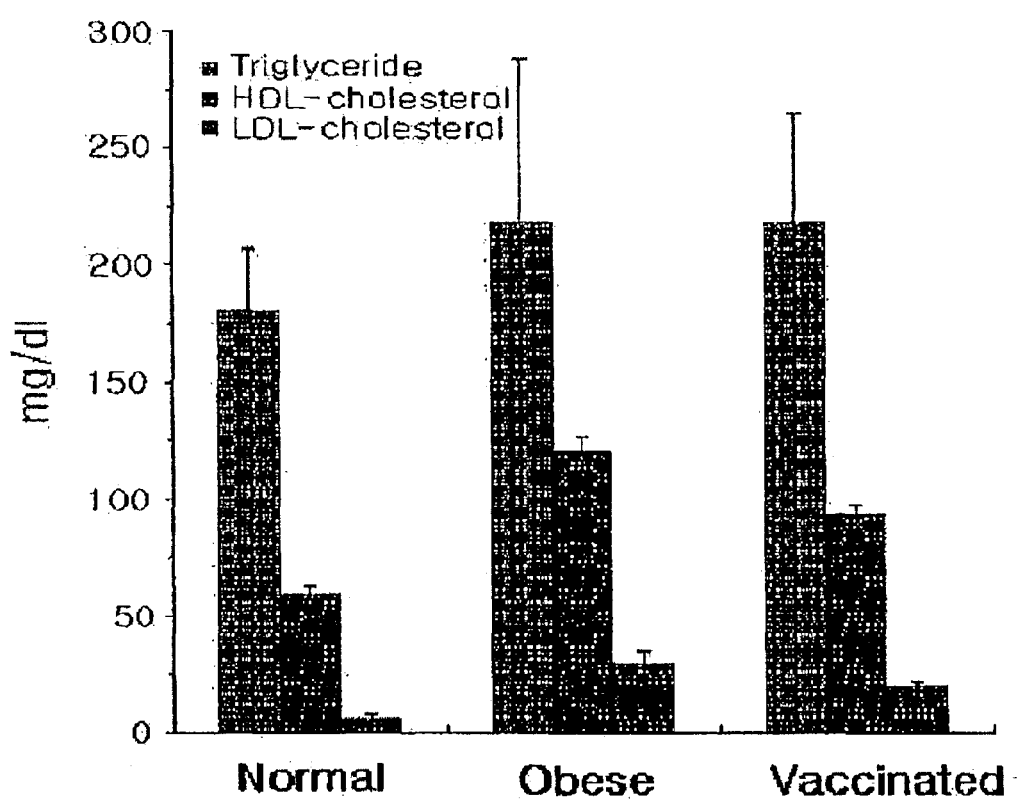
FIG. 12 represents the effect on the concentration of lipid in blood serum according to the injection of $PB1_4$ vaccine.

As depicted in Table 1 and FIG. 12, as the result of the induction of obesity, it was confirmed that there was no significant difference in the content of cholesterol of both the test group and the control did not increase whereas overall blood concentration of total cholesterol, HDL-C and LDL-C increased in small amount (FIG. 12).

While the present invention has been particularly shown and described with reference to particular examples thereof, it will be understood by those skilled in the art that various change in form and details may be conceived, therefrom without departing from the spirit and scope of the present invention as defined by the appended claim.

What is claimed is:

1. An isolated concatemer of peptides, wherein said concatemer comprises two (2) to about fifteen (15) peptides that each have the amino acid sequence of SEQ ID NO:1.

2. The concatemer of claim 1, wherein said concatemer comprises four (4) peptides that each have the amino acid sequence of SEQ ID NO:1.

3. An isolated concatemer of peptides, wherein said concatemer comprises two (2) to about fifteen (15) peptides that each have the amino acid sequence of SEQ ID NO:2.

4. The concatemer of claim 3, wherein said concatemer comprises four (4) peptides that each have the amino acid sequence of SEQ ID NO:2.

5. An isolated concatemer of peptides, wherein said concatemer comprises two (2) to about fifteen (15) peptides that each have the amino acid sequence of SEQ ID NO:3.

6. The concatemer of claim 5, wherein said concatemer comprises four (4) peptides that each have the amino acid sequence of SEQ ID NO:3.

7. A composition for the treatment of obesity, said composition comprising a peptide selected from the group consisting of a concatemer of peptides, wherein said concatemer comprises two (2) to about fifteen (15) peptides that each have the amino acid sequence of SEQ ID NO: 1, a peptide having the amino acid sequence of SEQ ID NO: 2, a peptide having the amino acid sequence of SEQ ID NO: 3, and mixtures thereof admixed with a carrier.

8. The composition according to claim 7, said composition is administered by intradermal injection.

9. The composition according to claim 7, wherein said composition is selected from the group consisting of tablets, pills, granules, cachets, elixirs, suspensions, emulsion, solution, syrups, aerosols, soft or hard gelatin capsules, sterilized injectable solution and sterilized powder.

10. A composition for the treatment of obesity, said composition comprising a concatemer of a peptide selected from the group consisting of a peptide having the amino acid sequence of SEQ ID NO:1, a peptide having the amino acid sequence of SEQ ID NO:2, a peptide having the amino acid sequence of SEQ ID NO:3, and mixtures thereof admixed with a carrier.

11. The composition according to claim 10, said composition is administered by intradermal injection.

12. The composition according to claim 10, wherein said composition is selected from the group consisting of tablets, pills, granules, cachets, elixirs, suspensions, emulsion, solution, syrups, aerosols, soft or hard gelatin capsules, sterilized injectable solution and sterilized powder.

13. A process for preparing a a concatomer of peptides, wherein said concatemer comprises two (2) to about fifteen (15) peptides that each have an amino acid sequence selected from the group consisting of SEQ ID NO:1, SEQ ID NO:2, and SEQ ID NO:3 comprising:

i) inserting into a vector a nucleic acid encoding a concatomer of peptides, wherein said concatemer comprises two (2) to about fifteen (15) peptides that each have an amino acid sequence selected from the group consisting of SEQ ID NO:1, SEQ ID NO:2, and SEQ ID NO:3;

ii) transforming host cells with the vector obtained in i);

iii) culturing said transformed host cells under conditions that permit expression of the inserted nucleic acid and formation of the encoded concatemer of peptides; and iv) isolating said concatemer of peptides from the host cell.

* * * * *

UNITED STATES PATENT AND TRADEMARK OFFICE
CERTIFICATE OF CORRECTION

PATENT NO. : 6,825,318 B2
DATED : November 30, 2004
INVENTOR(S) : Kim et al.

It is certified that error appears in the above-identified patent and that said Letters Patent is hereby corrected as shown below:

Column 14, Line 25, replace "

| HDL-C |  |
|---|---|
| 59±3.4 |  |
| 92±4.7 | 20±1.7 |
| 119±7.5 | 30±4.5 |

"

with --

| HDL-C | LDL-C |
|---|---|
| 59±3.4 | 6±1.2 |
| 92±4.7 | 20±1.7 |
| 119±7.5 | 30±4.5 |

--

Signed and Sealed this

Twenty-second Day of March, 2005

JON W. DUDAS
*Director of the United States Patent and Trademark Office*

SEQUENCE LISTING

<160> NUMBER OF SEQ ID NOS: 16
<210> SEQ ID NO 1
<211> LENGTH: 15
<212> TYPE: PRT
<213> ORGANISM: Artificial Sequence
<220> FEATURE:
<223> OTHER INFORMATION: Mimetic peptide for apolipoprotein B-100

<400> SEQUENCE: 1

Arg Asn Val Pro Pro Ile Phe Asn Asp Val Tyr Trp Ile Ala Phe
 1               5                  10                  15

<210> SEQ ID NO 2
<211> LENGTH: 15
<212> TYPE: PRT

```
<213> ORGANISM: Artificial Sequence
<220> FEATURE:
<223> OTHER INFORMATION: Mimetic peptide for apolipoprotein B-100

<400> SEQUENCE: 2

Arg Phe Arg Gly Leu Ile Ser Leu Ser Gln Val Tyr Leu Asp Pro
 1               5                  10                  15

<210> SEQ ID NO 3
<211> LENGTH: 15
<212> TYPE: PRT
<213> ORGANISM: Artificial Sequence
<220> FEATURE:
<223> OTHER INFORMATION: Mimetic peptide for apolipoprotein B-100

<400> SEQUENCE: 3

Ser Val Cys Gly Cys Pro Val Gly His His Asp Val Val Gly Leu
 1               5                  10                  15

<210> SEQ ID NO 4
<211> LENGTH: 23
<212> TYPE: DNA
<213> ORGANISM: Artificial Sequence
<220> FEATURE:
<223> OTHER INFORMATION: Oligonucleotide for the construction of BL or
      LB cassette

<400> SEQUENCE: 4
tcgaccgtaa tgttcctcct atc                                             23

<210> SEQ ID NO 5
<211> LENGTH: 28
<212> TYPE: DNA
<213> ORGANISM: Artificial Sequence
<220> FEATURE:
<223> OTHER INFORMATION: Oligonucleotide for the construction of BL or
      LB cassette

<400> SEQUENCE: 5
atcattgaag ataggaggaa cattacgg                                        28

<210> SEQ ID NO 6
<211> LENGTH: 29
<212> TYPE: DNA
<213> ORGANISM: Artificial Sequence
<220> FEATURE:
<223> OTHER INFORMATION: Oligonucleotide for the construction of LB
      cassette

<400> SEQUENCE: 6
ttcaatgatg tttattggat tgcattcta                                       29

<210> SEQ ID NO 7
<211> LENGTH: 24
<212> TYPE: DNA
<213> ORGANISM: Artificial Sequence
<220> FEATURE:
<223> OTHER INFORMATION: Oligonucleotide for the construction of LB
      cassette

<400> SEQUENCE: 7
agcttagaat gcaatccaat aaac                                            24

<210> SEQ ID NO 8
<211> LENGTH: 28
<212> TYPE: DNA
<213> ORGANISM: Artificial Sequence
```

```
<220> FEATURE:
<223> OTHER INFORMATION: Oligonucleotide for the construction of BL
      cassette

<400> SEQUENCE: 8
ttcaatgatg tttattggat tgcattcc                                    28

<210> SEQ ID NO 9
<211> LENGTH: 23
<212> TYPE: DNA
<213> ORGANISM: Artificial Sequence
<220> FEATURE:
<223> OTHER INFORMATION: Oligonucleotide for the construction of BL
      cassette

<400> SEQUENCE: 9
tcgaggaatg caatccaata aac                                         23

<210> SEQ ID NO 10
<211> LENGTH: 24
<212> TYPE: DNA
<213> ORGANISM: Artificial Sequence
<220> FEATURE:
<223> OTHER INFORMATION: Upper strand of the leader cassette

<400> SEQUENCE: 10
gatccgatga tgatgacaag atcg                                        24

<210> SEQ ID NO 11
<211> LENGTH: 24
<212> TYPE: DNA
<213> ORGANISM: Artificial Sequence
<220> FEATURE:
<223> OTHER INFORMATION: Lower strand of the leader cassette

<400> SEQUENCE: 11
tcgacgatct tgtcatcatc atcg                                        24

<210> SEQ ID NO 12
<211> LENGTH: 6
<212> TYPE: PRT
<213> ORGANISM: Artificial Sequence
<220> FEATURE:
<223> OTHER INFORMATION: Enterokinase cleavage site

<400> SEQUENCE: 12

Asp Asp Asp Asp Lys Ile
 1               5

<210> SEQ ID NO 13
<211> LENGTH: 52
<212> TYPE: DNA
<213> ORGANISM: Artificial Sequence
<220> FEATURE:
<223> OTHER INFORMATION: Upper strand of the LB cassette

<400> SEQUENCE: 13
tcgaccgtaa tgttcctcct atcttcaatg atgtttattg gattgcattc ta         52

<210> SEQ ID NO 14
<211> LENGTH: 52
<212> TYPE: DNA
<213> ORGANISM: Artificial Sequence
<220> FEATURE:
<223> OTHER INFORMATION: Lower strand of the LB cassette

<400> SEQUENCE: 14
```

-continued

```
agcttagaat gcaatccaat aaacatcatt gaagatagga ggaacattac gg        52

<210> SEQ ID NO 15
<211> LENGTH: 51
<212> TYPE: DNA
<213> ORGANISM: Artificial Sequence
<220> FEATURE:
<223> OTHER INFORMATION: Upper strand of the BL cassette

<400> SEQUENCE: 15
tcgaccgtaa tgttcctcct atcttcaatg atgtttattg gattgcattc c         51

<210> SEQ ID NO 16
<211> LENGTH: 51
<212> TYPE: DNA
<213> ORGANISM: Artificial Sequence
<220> FEATURE:
<223> OTHER INFORMATION: Lower strand of the BL cassette

<400> SEQUENCE: 16
tcgaggaatg caatccaata aacatcattg aagataggag gaacattacg g         51
```